United States Patent
Schilling

(10) Patent No.: US 7,638,343 B2
(45) Date of Patent: Dec. 29, 2009

(54) METHOD TO IDENTIFY OR EVALUATE COMPOUNDS USEFUL IN THE FIELD OF FRAGRANCES AND AROMAS

(76) Inventor: Boris Schilling, Rigiblickstrasse 9, CH-8934 Knonau (CH)

( * ) Notice: Subject to any disclaimer, the term of this patent is extended or adjusted under 35 U.S.C. 154(b) by 22 days.

(21) Appl. No.: 11/632,976

(22) PCT Filed: Jul. 15, 2005

(86) PCT No.: PCT/CH2005/000412
§ 371 (c)(1), (2), (4) Date: Apr. 30, 2007

(87) PCT Pub. No.: WO2006/007752
PCT Pub. Date: Jan. 26, 2006

(65) Prior Publication Data
US 2007/0238187 A1    Oct. 11, 2007

(30) Foreign Application Priority Data
Jul. 21, 2004    (GB)    ................... 0416239.2

(51) Int. Cl.
*G01N 1/22*    (2006.01)
(52) U.S. Cl. ................ 436/181; 436/174; 422/83; 422/84; 422/88; 73/23.3
(58) Field of Classification Search ............ 422/83, 422/84, 88, 89, 90; 436/174, 178; 73/23.3, 73/23.34, 23.35, 23.41, 23.42; 426/181
See application file for complete search history.

(56) References Cited

U.S. PATENT DOCUMENTS

| | | | |
|---|---|---|---|
| 3,902,851 A | 9/1975 | Dravnieks, et al. | |
| 5,042,501 A | 8/1991 | Kenny et al. | |
| 5,479,815 A * | 1/1996 | White et al. | 73/23.3 |
| 5,869,344 A * | 2/1999 | Linforth et al. | 436/173 |
| 7,052,468 B2 * | 5/2006 | Melker et al. | 600/532 |

FOREIGN PATENT DOCUMENTS

| | | |
|---|---|---|
| EP | 0 669 531 A | 8/1995 |
| EP | 0 819 937 A | 1/1998 |
| EP | 0 883 049 A | 12/1998 |

OTHER PUBLICATIONS

Mayr, D., et al. "Breath-by-breath analysis of banana aroma by proton transfer reaction mass spectrometry"; International Journal of Mass Spectrometry, Elsevier Science Publishers, Amsterdam, NL; vol. 223-224, Jan. 15, 2003, pp. 743-756.
Harvey, B. A., et al. "Real time breath and headspace analysis of flavour volatiles"; European Journal of Pharmaceutics and Biopharmaceutics, Elsevier Science Publishers, Amsterdam, NL, vol. 55, No. 3, May 2003, pp. 261-269.
S. Ali, et al. "In-Vivo Analysis of Aroma Release While Eating Food: A Novel Set-Up For Monitoring On-Line Nosespace Air"; 1st International Conference on Proton Transfer Reaction Mass Spectroscopy and Its Applications, 2003, pp. 161-164.
Benoit, F. M., et al. "Breath Analysis By Atmospheric Pressure Ionization Mass Spectrometry", Analytical Chemistry, American Chemical Society, Columbus, OH, United States, vol. 55, 1983, pp. 805-807.
Karpe, P., et al. "Thermal desorption-gas chromatography-mass spetrometry-flame ionization detection-sniffer multi-coupling: A device for the determination of odorous volatile organic compounds in air"; Journal of Chromatography A, Elsevier, Amsterdam, NL; vol. 708, No. 1, Jul. 28, 1995.

* cited by examiner

*Primary Examiner*—Jill Warden
*Assistant Examiner*—Dwayne K Handy
(74) *Attorney, Agent, or Firm*—Curatolo Sidoti Co., LPA; Joseph G Curatolo; D. Ari Sherwin

(57) ABSTRACT

The invention relates to methods of identification or evaluation of compounds useful in the field of fragrances and aromas (the volatile part of a flavor). Methods according to the invention take into account the occurrence of enzymatic metabolism in the human respiratory tract, including the oral and in particular the nasal cavity.

10 Claims, No Drawings

METHOD TO IDENTIFY OR EVALUATE COMPOUNDS USEFUL IN THE FIELD OF FRAGRANCES AND AROMAS

CROSS REFERENCE TO RELATED APPLICATION

This application is a national stage application of International Application No. PCT/CH2005/000412, filed 15 Jul. 2005, which claims the benefit of Application No. GB 0416239.2, filed 21 Jul. 2004, from which applications priority is claimed.

BACKGROUND

The invention relates to methods of identification or evaluation of compounds useful in the field of fragrances and aromas (the volatile parts of flavour). Methods according to the invention take into account the occurrence of enzymatic metabolism in the human respiratory tract, including the oral and in particular the nasal cavity.

Compounds which reach the nasal cavity and exert a particular effect, such as binding to receptors, which is a prerequisite to perceive olfactory stimuli, are constantly changing their environment and different physico-chemical specificities are of advantage and disadvantage in each phase of their lifetime. First, the compound is in a base, e.g. as part of a fragrance oil where a particular vapour pressure is required to be volatile. Depending on the type of odour release (directly transfer in headspace, or dispersion, e.g. as aerosols) different properties are of advantage for the constituents of the perfume mixture. While a high vapour pressure is often desirable, the compound has to be able to readily dissolve into the nasal mucosal fluid covering the neuronal cells. Finally, the compound needs to bind and activate receptor proteins. For most of the journey from base to receptor, the odorant compounds appear to remain unchanged. However, the situation seems to be more complicated. It has been speculated that metabolism is rendering odorant compounds inactive to make them more water-soluble and facilitate clearance from the nasal epithelium.

Furthermore, it has been speculated that, for some fragrance ingredients, the compound that is directly responsible for the perception of the odour (the odorant), is not the fragrance ingredient itself. Instead, the fragrance ingredient may merely be a non-odorant precursor that forms, as a metabolite, the actual odorant which activates the olfactory receptor to result in olfactory perception. Said odorant metabolites may be formed enzymatically in the human respiratory tract, particularly in the epithelium of the human nose.

Metabolism of such precursors that are substrates of enzymes may occur prior to receptor binding in the fluidic mucus or in cells lining the cavity or it may occur after receptor activation. This may change their various abilities that influence odorant perception, including its physico-chemical properties (for example solubility in mucosal fluid) and activation of the receptor. The metabolite(s) may have chemical and/or physical properties which are of advantage for interaction with receptors, other enzymes and/or odorant binding proteins. Substrates may be odorant compounds or non-odorant compounds. In the case of the latter, one or more metabolite of the substrate may be an odorant, and/or have the above-mentioned properties.

Metabolism may inactivate or activate receptor ligands. Compounds of interest may be agonists, antagonists, enzyme substrates, enzyme inhibitors, and allosteric regulators of receptors or enzymes. The metabolites may compete, for example, for receptor binding, interact with additional receptors and enzymes, and/or modulate the activity and sensitivity of receptors and enzymes. The metabolites generated from substrates of metabolic enzymes may have properties that enable them to interact with receptors and enzymes and these metabolites may in fact be primarily responsible for the perceived quality and effects of flavour and fragrance ingredients and/or compete with their substrates for receptor interaction, and in particular for receptor activation.

However, metabolism involving odorant compounds in the human respiratory tract, particularly in the olfactive mucosa, has not been shown in vivo.

The present invention employs known analytical methods to provide a method of identifying, analysing or evaluating test compounds useful in the field of fragrances and aromas.

Compounds useful in the field of fragrances and aromas may be fragrance and aroma compounds as such, but also modulators of their perception. Modulators are compounds that influence the olfactive perception of odorant compounds. A modulator may result in changes of intensity (overall enhancer or masking agent), quality (change of olfactive note, enhancing or masking of particular notes), duration/longevity of perception, or combinations of these. A modulator may enhance the overall perception of a particular odorant or mixture of odorants, or a particular olfactive quality/note. A modulator may reach these effects by modulating, influencing or regulating metabolic reactions in the respiratory tract. A modulator may enhance or suppress metabolism, for example by affecting the enzyme directly. Instead of influencing enzymes, a modulator may affect (activate or block) one or more receptors to reach an enhancing or blocking/masking effect, or to influence the quality and olfactive note of perception. A modulator may extend the "life-time" or duration of the effect of an odorant by hindering or suppressing its usual metabolism and thereby enhancing its intensity or longevity. A similar enhancing effect will be caused by a compound that positively influences the rate of enzymatic activity, provided that the substrate that is metabolised to form its metabolite is not odorant (or less odorant) than its odorant metabolite. Modulators may suppress metabolism occurring in the human respiratory tract and/or change the olfactive quality of single odorants.

SUMMARY

In a first aspect of the invention, the invention is directed to a method of identifying or evaluating compounds, wherein either the compound or at least one of its metabolite is an odorant, or a precursor of an odorant, or a modulator of the perception of an odorant, comprising
a) Providing a saturated headspace of a test compound
b) Inhalation of said saturated headspace by a human test subject
c) Emission of exhaled breath by the human test subject
d) Analysis of the exhaled breath in real time by a detection method selected from Metabo-GM, Metabospace, and Proton Transfer Reaction Mass Spectrometry (PTR-MS).

The saturated headspace may be provided as described in the examples hereinunder.

DETAILED DESCRIPTION

In one particular embodiment, the compound is inhaled and exhaled through the nose. In another embodiment, the compound is inhaled through the nose and exhaled through the mouth. In another particular embodiment, the compound is inhaled through the mouth and exhaled through the nose. In still another embodiment, the compound is inhaled and exhaled through the mouth.

In another particular embodiment, Metabospace or PTR-MS are used. Surprisingly, applicant found that metabolites of volatiles are detected instantaneously using these methods. This could not have been predicted. It is even possible in some cases to determine the location within the human respiratory tract of the biotransformation enzyme by performing the inhalation/exhalation protocols as described above and analysing the results, as shown in the examples herein-below.

In still another particular embodiment, in addition to the analysis by Metabo-GM, Metabospace, and Proton Transfer Reaction Mass Spectrometry (PTR-MS), an olfactometer analysis may be performed.

By the methods according to the invention, metabolites may be identified that result from compounds (substrates) which are metabolised by an enzyme. These metabolites may be odorant compounds themselves. Likewise the substrates may be fragrance ingredients that may be odorants themselves, or they may be odourless or weakly odorant precursors that provide an odour perception only after metabolism by way of their metabolite. Precursors and metabolites may have a different olfactive note. The actual olfactive note corresponding to a certain chemical structure is important for lead finding. Methods not taking into account metabolism may result in incorrect structure-function/olfactive note relationships that hinder correct lead finding. Inventive methods provide for efficient lead finding since they allow lead finding to be based on the correct structures that activate the receptor and trigger the olfactive sensation, rather than the precursor compound from which the odorant results. To illustrate this, compound "A" (fragrance ingredient) has a particular olfactive note described by a perfumer. A is metabolised to compound "B" (odorant) in the nose and B is responsible for the particular note generally associated with compound A, by activating one or several olfactory receptors which are required to perceive the olfactive sensation as described by the perfumer.

A modulator may be identified by its effects on a metabolic reaction as detected by the methods of the present invention, i.e. by changing (e.g. enhancing or suppressing) the quantity, intensity or quality of olfactive perception. A modulator may be identified by a change in quantity of an odorant compound, which may be caused by the modulator's influence on the rate of metabolism, as measured by reduction of substrate or formation of metabolite by the analysis and detection methods described herein-under. In addition, modulators may change the intensity or olfactive quality of a single odorant, which may be identified or characterised by use of an olfactometer. To illustrate this further, a precursor compound may be partially metabolised in the human nose to form a metabolite compound, with both compounds being present in the nose in parallel. Both compounds may have different olfactive notes, which may account for the broad olfactive description assigned to some single fragrance or aroma compounds. The present invention makes lead finding for particular olfactive notes easier and allows comparing olfactive notes of both a given compound and its potential metabolite. In another setup a test compound and its metabolite can be compared in presence and absence of compounds that modulate metabolism.

The detection and analysis methods described below can be used to identify a suppressor of metabolism (for example an inhibitor or competitive substrate of a metabolic enzyme) as follows. A standard substrate is selected and test compounds are analysed for their ability to influence or modulate the formation of metabolite(s) detected with said methods. A suppressor is identified by a reduction in the formation of metabolite(s) from inhaled substrates compared to the control without suppressor. A suppressor may be an inhibitor or a competing substrate. The term inhibitor is meant to include compounds which act as negative allosteric regulators of enzymatic activity. An inhibitor and a competing substrate may be distinguished from each other by the presence or absence of signals resulting from formation of additional metabolites formed by metabolism of a competing substrate.

The present invention may also be used as an evaluation method to confirm in vivo the data that results from in vitro analysis, in particular in vitro assays using metabolic enzymes from the human respiratory tract.

Detection and Analysis Methods

Detection and analysis methods include Metabo-GM, Metabospace, and Proton Transfer Reaction Mass Spectrometry (PTR-MS). One or more of these methods may be combined. In particular, PTR-MS may be used in addition to Metabospace.

In addition to one or more of Metabo-GM, Metabospace and PTR-MS, an Olfactometer analysis may be performed to further characterise the effects of modulators.

Metabospace

The "Metabospace" technology allows real-time detection and analysis of in vivo generated metabolites (exhaled volatiles) starting from compounds of interest. First, a test subject inhales the saturated headspace of a volatile compound. The saturated headspace may be provided as described in the examples herein-below. The breath is exhaled directly into a glass funnel, which works as interface to an analysis device where mass spectra are recorded by a quadrupole mass spectrometer equipped with an atmospheric pressure chemical ionization (APCI) ion source with a modified interface which allows the measurement of fast dynamic changes of volatiles as described in Grab, W., and Gfeller, H. In: ACS Symposium Series 763—Flavor Release (Roberts, D. D., and Taylor, A. J., Eds.) American Chemical Society, Washington, D.C. (2002). The procedure may be performed for example as described further in the examples herein below.

Mass spectrum scans detect the entire range of pseudomolecular ions as well as ions of fragments of molecules. If candidate metabolites are already known, e.g. from in vitro data, the mass chromatogram corresponding to the pseudomolecular ion can be directly visualized together with the chromatogram for the substrate. Acetone is always present in human breath and can be used to show the respiration pattern. Mass spectrum scans of volatiles either exhaled from the nasal or the oral cavity are recorded in narrow time spans, for example twice per second, to follow changes in breath composition as a function of time and respiration cycles. Usually, a series of scans are done to detect other ions that may be linked to the substrate and/or metabolites, which can e.g. be derived from fragments of the substrate and/or the metabolites, as is well-known to the person skilled in the art. Various mass spectrum scans are performed as is well known in the art. In the present invention, a large number of mass spectrum scans are be recorded by the mass spectrometer (for example 2 scans per second). The total ion chromatogram (TIC) gives the total of signals. Individual signals, e.g. the pseudomolecular ion $[M+H]^+$ for acetone at m/z 59, may be singled out and analysed over time in so-called "mass chromatograms". Metabolites appear as additional signals in scans, and specific signals are followed over time in respective mass chromatograms. During the first inhalation/exhalation cycles, scans are analysed for ions which are present in exhalations following the inhalation of surrounding air (blank, background) and are not derived from the test compound or from metabolites. It is well known in the art how to identify unknown signals. Depending on the chemistry of the test compound and the possible metabolic reactions which can take place, particular ions are expected to occur if such metabolism takes place. To narrow down the possibilities, a hypothesis based on the test compound (enzyme substrate) and potential biotransformation reactions resulting in metabolites is used. For example, metabolites that result from reactions of the test compound with oxidizing enzymes belonging to the group of CYP enzymes may undergo metabolism including hydroxylation or epoxidation reactions, and specific signals for such metabolites may be generally found at the m/z number of the substrate plus 16. Other reactions catalyzed by CYP enzymes include the demethylation of a test compound, e.g. demethylation of N-methyl or O-methyl (methoxy) groups, and specific signals may be generally found at m/z of the substrate minus 14. Combinations of reactions can take place, such as multiple hydroxylation reactions, a combination of hydroxylation and demethylation, etc. It is apparent to the skilled person how to analyse these to identify the metabolite(s). If a definite identification is not possible based on expected derivatives and comparisons to mass spectral data contained in analytical databases, a series of proposed compounds may be synthesized chemically in order to confirm the hypothetical structure of the metabolite(s). Preferably, formation of metabolites is confirmed by an alternative in vivo method, such as PTR-MS or METABO-GM. Since exhaled material is absorbed on a resin in the case of METABO-GM, it is possible to desorb the compounds and isolate single constituents by preparative GC, and subsequently purified compounds may be analyzed by nuclear magnetic resonance ($^1$H-NMR and $^{13}$C-NMR) in order to elucidate their chemical structure.

In the present invention, volatile compounds are presented to a test subject to exhale and the exhaled breath (after potential metabolism occurring in the human respiratory tract) is analysed by performing mass spectrum scans which are recorded twice per second. At this rate, it is possible to follow changes in breath composition as a function of time and respiration cycles.

Proton Transfer Reaction Mass Spectrometry (PTR-MS)

PTR-MS is commonly used for the analysis of the aroma release and retronasal transport from the oral cavity to the nose (e.g.: Ali et al. (2003) In vivo analysis of aroma release while eating food: a novel set-up for monitoring on-line nosespace air. In: *1st International Conference on Proton Transfer Reaction Mass Spectrometry and Its Applications, 2nd Edition* (A. Hansel, T. Märk, Eds.) pp 161-164).

In the context of the present invention, PTR-MS allows not only the detection of compounds in real-time, but in addition, the measured count rates of individual compounds can be directly used to determine absolute headspace concentrations. PTR-MS may be carried out as described for Metabospace herein-above.

PTR-MS is a volatile organic compound detector, and different versions of such a device are available (IONICON Analytik GmbH, Innsbruck, Austria). The device consists mainly of three parts, the ion source which converts water vapour by plasma discharge into $H_3O^+$ ions; a drift tube where proton transfer reactions to trace constituents in the air occur; and the ion detector providing sensitive detection of mass selected ions.

Similar to the APCI used in Metabospace, the proton transfer results in the formation of a pseudomolecular ion $[M+H]^+$ which is analysed in a downstream quadruple mass spectrometer. The technology, specificities and characteristics are described in detail in: Lindinger et al. (1998) *Int. J. Mass Spectrometry and Ion Processes* 173:191. On-line analysis of volatile organic compounds at pptv levels by means of Proton-Transfer-Reaction Mass Spectrometry (PTR-MS) Medical applications, food control and environmental research; and references therein.

Metabo-GM

Exhaled compounds are trapped on a resin, followed by desorption of bound material and analysis by gas chromatography, linked to mass spectrometry (GC-MS).

A test subject inhales a saturated headspace of a known compound, and the exhaled air is trapped on an appropriate adsorbent resin which is contained in a glass tube that is connected directly to at least one nostril.

Suitable resins are Tenax™ TA (Scientific Instrument Services Inc., US), which is a porous polymer resin based on 2,6-diphenylene oxide, and Tenax™ GR (Scientific Instrument Services Inc., US), which is a composite material of Tenax™ TA and 30% graphite. Instead of these particular resins, any resin capable of trapping volatiles from air may be used, which may be easily tested with test compounds by the skilled person.

A glass tube of appropriate outer diameter, for example approximately 16 mm diameter, is used. Said tube is filled with a resin (e.g. 0.2-2 grams, preferably 0.5 grams, depending on the volume of exhaled air to be analyzed) and silane-treated glass wool (Supelco, U.S.). Said wool is used at both sides of the resin to keep the resin in the middle of the tube (the glass tube needs to fit the adaptor at the Thermoextractor as described below, which defines the required outer diameter).

One of the test subject's nostril is blocked. Through the open nostril, the test subject inhales the test compound, and exhales through a tube that contains the resin. Alternatively, both nostrils are connected to the tube, or the tube is connected to vacuum and exhaled air channelled through a glass funnel to be adsorbed on the resin.

Trained test subjects are usually able to inhale/exhale a fairly constant volume. To ensure a constant volume, plastic bags of different sizes can easily be connected to the outlet of the glass tube in order to control the volume of air exhaled. Optionally, a flow meter is installed to control the velocity of exhalation in addition to the volume (suitable bags for volume control are available e.g. from Restek Corp., US).

In a first step, the test compound is placed in a container, for example a glass container of 0.25-2 litre volume, preferably 0.5-1 litre.

In a second step, saturated headspace is slowly inhaled and exhaled air is trapped as described above. This step usually is repeated several times to increase the concentration of the volatile and metabolites on the adsorption resin. The optimal repeat rate needs to be adjusted to each test compound depending on vapour pressure and extent of metabolism.

In a third step, a Thermoextractor (e.g. from GERSTEL, Germany) is used to transfer the compounds trapped on the resin to an analysis tube of smaller diameter (e.g. approximately 6 mm, which fits the Thermoextractor adaptor and fulfils standards for auto sampler loading). The analysis tube can be loaded into an auto sampler in the subsequent analysis. This step also removes water from the sample that may interfere with the subsequent analysis.

In the fourth step, the analysis tube is placed in an auto sampler (e.g. Thermodesorption Autosampler TDS-A, GERSTEL, Germany) and a computer-controlled analysis sequence started.

The analysis encompasses 3 steps.

First, the sample is cryo-focused in the GC injection liner by the thermal desorption of resin-bound compounds (e.g. Thermodesorption system TDS, GERSTEL, Germany) and concentrated in a Cryo-Trap (e.g. Cooled Injection System CIS, cooled with liquid nitrogen, GERSTEL, Germany) for subsequent heating and transfer to the separation column.

Then the compounds contained in the sample are separated by GC (e.g. Hewlett Packard Model 5890, equipped with a DB-Wax column, Macherey-Nagel, Germany) and analyzed by mass-spectrometry (e.g. Hewlett Packard Model 5972). The GC column is selected according to the required separation properties in view of the compounds of interest, as is well-known in the art.

Last, the MS patterns of the detected compounds are compared to databases to determine the chemical structure of the compounds.

Alternatively, compounds already known as modulators of the enzymatic activity of biotransformation enzymes (e.g. suppressors), or compounds shown to be such by inventive methods described herein-above, are inhaled simultaneously or prior to inhalation of the test compound of interest. Since the test compound and its metabolites are detected by Metabo-GM, this method allows determining the extent of metabolism and the influence of modulators of biotransformation enzyme in vivo.

Modulators, suppressors, enhancers which have been identified by any of the above described methods can be tested for their effect on the perception of single fragrance compounds and mixtures using a Cascade Olfactometer as described below.

Olfactometer Analysis

A particular odorant concentration by dilution of a saturated vapour phase can be achieved by employing an olfactometer. One or two olfactometers may be used.

Olfactometers, particularly the Olfactometer type described in EP0883049, may be used to identify a test compound as a modulator of the perception of fragrance and aroma compounds. It can be used to assess changes in intensity (threshold) and quality. It is used to determine the influences of modulators on olfactive perception, particularly when modulators of odorant metabolism or receptor antagonists are evaluated. A test subject smells a given test compound at a particular concentration from a sniffing port (e.g. a glass funnel) of the olfactometer and is rating the intensity and quality of the odour. Different dilutions of saturated headspace of the compound of interest are used (dilution may be with air, preferably with dry air). Though moistened air may also be used, often it appears to be negative for olfactive perception. Alternatively, a mixing chamber allows to add a second compound (for example to identify a modulator) to the diluted headspace reaching the sniffing port.

The cascade olfactometer employs more than one olfactometer simultaneously. One provides a reference while a second provides the test compound at a different concentration or in combination with a second test compound to be analysed for its effects on the first. The reference may be, for example a standard of a particular odorant, a test compound used at a fixed concentration, a particular odorant mixture, or a particular mixture of odorant and modulator. The second test compound may be a potential modulator or compound to be analysed for masking, blocking or enhancing effects.

The olfactometer analysis is particularly of interest in methods of the present invention after having performed the detection and analysis methods described herein-above, and when the sensory quality and/or quantity (intensity; olfactory threshold) of substrate and metabolite are different. The olfactometer analysis is performed as follows: During analysis the concentration of the test compounds (for example a given substrate and a potential modulator) are varied. If several substrates of the same biotransformation enzyme are known these may all be tested as described herein-below for confirmation. To be able to validate the sensory effect caused by the modulator, the test compound (substrate or respective metabolite(s) or both) must be odorant compounds. Concentration and ranges for the test compounds are evaluated before the experiments are conducted with a number of test subjects. Test subjects are asked to smell a series of randomly altered samples through the sniffing port and rate either intensity and/or quality of the presented sample. This can be efficiently done by a computer-controlled protocol. Test subjects may also asked to compare these to a "standard sample" which is provided through a second sniffing port and indicate differences.

Different sensory evaluation protocols can be used to described quantity (intensity) and/or quality and/or effects of test compounds, standard odours, odour mixtures, etc. A protocol well known to the skilled person is the labeled-magnitude scales (LMS) protocol, where test subjects are asked to indicate their ratings, as is well known in the field of sensory analysis. The LMS is a semantic scale of perceptual intensity characterised by a quasi-logarithmic scaling of its verbal labels, as described by Green et al. (1996) *Chemical Senses* 21:323-334. The positions of the verbal labels on the LMS, as percentage of full scale length, are: barely detectable, 1.4; weak, 6.1; moderate, 17.2; strong, 53.2; strongest imaginable, 100.

The just-noticeable-difference (JND) protocol is also used in the field of sensory analysis and is easily adaptable to evaluate effects as described in this invention by a person skilled in sensory psychophysics. The test subjects are asked to compare the presented stimulus containing a test compound to a stimulus which has been presented previously in the study, or to a stimulus which is presented simultaneously at a second olfactometer (the reference). The Cascade Olfactometer setup is preferred where two olfactometers are used simultaneously, one providing the reference. The entire procedure in the JND protocol is computer controlled, and test subjects are asked to indicate their ratings of a presented stimulus to the reference. Possible answers with respect to the relative intensity are presented as reference points on a scale (e.g. "equal", "weaker", "much weaker", "stronger", "much stronger") and the test subjects marks the answer with respect to the intensity of the presented stimulus (e.g. the test compound, a mixture, test compound with modulator, etc.) along the scale that is visualized on the computer screen, with a mouse-click.

Modulator compounds (for example suppressors of metabolism and in particular inhibitors of metabolic enzymes) are identified by their dose-dependent effect on the intensity and/or quality of odorants. These odorants may be for example substrates of said biotransformation enzymes. Characterised by their effects as identified by olfactometer analysis, modulators may be for example masking agents that mask the perception of a particular test compound or a composition of test compounds, or a particular olfactive quality of a test compound. A modulator as identified by olfactometer analysis can be a test compound or a metabolite thereof. Furthermore, a modulator as identified during olfactometer analysis can influence the perception of a test compound at one or several levels, such as for instance at the level of metabolism (modulator of enzymatic activity), at the level of olfactory receptors (modulator is an agonist, or an antagonist=blocker, or an allosteric regulator) and/or at the level of the signal transduction cascade (modulator of activity of components of the signal transduction cascade, e.g. the CNG channel).

For example, test subjects are asked to rate the intensity of an odorant volatile test compound when randomly presented with different concentrations (dilutions of saturated headspace) of a second test compound. Preferably, the second test compound is chosen from odourless compounds, or a compound with a high odour threshold. Thus, this odourless/ weakly odorant second test compound may be identified as a modulator for example by its influence on the perceived intensity of the odorant test compound.

In another example, said second test compound can be identified as a modulator by its ability to alter the quality of another volatile odorant test compound.

The identified effects of test compounds (e.g. modulating activity) may be used to define lead structures in order to design, search for and identify derivatives useful for the field of odorants.

The choice of odorants which are e.g. substrates of biotransformation enzymes can be critical for success of the evaluation procedure and knowledge about the physicochemical properties, such as vapor pressure, olfactory perception threshold, logP (clogP) are indispensable, and the technologies required to conduct the appropriate measurements are obvious to the person skilled in the art.

Leads

After identifying a compound by a method according to the invention, the identified test compounds (which may be for example substrates or metabolites or modulators of a metabolic enzyme) may be used as leads and derivatives may be synthesised in order to find useful compounds of particular desired qualities of interest. The derivatives are again used as test compounds in a method according to the invention as described hereinabove. The procedure may be repeated until a compound of a particular desired olfactive note of interest, or a particular advantageous effect in combination with other odorant compounds is identified. The compounds of interest may be odorant compounds themselves, or they may have an effect on olfactive perception. The compounds may be metabolites or their precursors of odorants, the compounds may improve the performance of odorants, or suppress or mask the perception of undesired olfactive notes of odorant compounds. All these latter that have an effect on olfactive perception may or may not have an odour themselves.

EXAMPLES

Example 1

General Procedure Employing Metabospace

Metabospace is performed as described below.

A saturated headspace of a pure test compound A is prepared. For liquid compounds, this is achieved by soaking 5 blotter strips in the test compound and placing them in a glass flask (250 ml volume) closed with a glass plug and allowing to equilibrate for 20 minutes at room-temperature. Solid compounds may simply be added to a glass flask, preferably in a form with a large surface area.

In order to ensure that the test compound is pure and contains no contaminants, depending on the source, the test compound may have to be further purified, for example by flash chromatography.

To record background signals which are present in the breath of the individual test subject, the test subject inhales surrounding air, and exhales into a glass funnel that serves as an interface into the ionization chamber of a APCI-MS. This inhalation/exhalation is continued about 30 times without moving the nose away from the funnel.

Subsequently, the test subject inhales the prepared saturated headspace containing test compound A through the nose, and exhales through the nose directly into the glass funnel at the device. Without moving the nose away from the funnel, inhalation/exhalation is continued 30 times.

After a break of 5 minutes, the individual exhales again 30 times into the funnel to show changes in the background exhalation compared to the background recorded at the start. This is again repeated after 15 minutes, at which time the background (lacking the signal resulting from substrate and metabolite) usually is identical or very similar to the first background recording before exposure to the test compound.

In order to follow the respiration pattern and presence of compounds of interest such as the substrate and a metabolite, particular mass chromatograms are analysed.

To identify the metabolite of the test compound A in real time as it is produced in the human nose, the relative abundances of the following pseudomolecular ions are analysed: acetone ($[M+H]^+$ at m/z 59) which is always present in exhaled air from human beings, the test compound ($[M+H]^+$ chosen as appropriate), its metabolite(s) ($[M+H]^+$ chosen as appropriate); and the total ion chromatogram (TIC) of the recorded mass spectra (2 scans per second).

Example 2

Test Compound 2-methoxyacetophenone

The procedure is performed as described in example 1 with 2-methoxyacetophenone as test compound subject to the following modifications:

In order to start with a sample containing no 2-hydroxyacetophenone as contaminant, the commercially available quality (Fluka, Buchs, Switzerland) was further purified by flash chromatography.

The analysis as described in example 1 shows that following inhalation of 2-methoxyacetophenone which is detected at m/z 151, at m/z 137 a compound is detected which corresponds to 2-hydroxyacetophenone.

Example 3

Test Compound 2-methoxyacetophenone, Different Inhalation/Exhalation Protocols

The procedure is performed as described in example 2 with 2-methoxyacetophenone as test compound subject to the following modifications.

The inhalation/exhalation protocol was adjusted as follows. Room air (control) or saturated headspace of 2-methoxyacetophenone were inhaled either through the nose or the mouth, and exhaled either through the nose or the mouth. Two of the four possible variants are analysed both for test compound and a control=room air. In the first variant, inhalation and exhalation occur both through the mouth. In the second variant, inhalation occurs through the mouth and exhalation through the nose.

As regards the control, none of these inhalation/exhalation protocols produced the mass fragment indicative of the presence of 2-hydroxyacetophenone (the metabolite).

For the test compound, there is a clear difference between breathing protocols.

In the first variant, no signal corresponding to the metabolite is detected.

In the second variant, the presence of a signal (m/z 137) indicates the formation of 2-hydroxyacetophenone (metabolite).

This shows that the respiratory tract metabolism of 2-methoxyacetophenone takes place predominantly as a result of enzymatic activity in the nasal cavity.

Example 4

Comparison of Release of 2-hydroxyacetophenone in Exhaled Breath to Exhaled 2-methoxyacetophenone; Analysis of Signal Intensities, Retarded Release The procedure is performed as described in example 2. Intensities of mass chromatogram signals specific for the substrate 2-methoxyacetophenone and 2-hydroxyacetophenone (metabolite) and their decrease as a function of time (inhalation/exhalation cycles) are analysed.

The intensity of the signal specific for 2-methoxyacetophenone (m/z 151) decreases relatively quickly, within about 30 inhalation/exhalation cycles, while the signal specific for the metabolite 2-hydroxyacetophenone (m/z 137) is still near maximal intensity after 30 inhalation/exhalation recordings.

The detected retardation effect may be due to the higher water solubility of the metabolite that is formed in the aqueous mucus, resulting in a prolonged time span over which the metabolite is exhaled.

Example 5

Test Compound Ketanone (Methyl-Raspberry Ketone)

The procedure is performed as described in example 2, with ketanone (methyl-raspberry ketone) as test compound.

The analysis of signals shows that following inhalation of ketanone which is detected at m/z 179, a compound is detected at at m/z 165 which corresponds to 4(4-hydroxyphenyl)butan-2-one (raspberry ketone)(metabolite). This is believed to be due to demethylation of the methoxy group of the test compound by enzymes present in the respiratory tract.

4-(4-hydroxyphenyl)butan-2-one (raspberry ketone) is a signature compound for raspberry aroma and has a very low olfactory threshold. Ketanone is described as having some raspberry character, although being significantly less intense (Winter (1961) *Helv. Chim. Acta* 44:2110).

The example is repeated as described in example 4 and signal intensities are analysed. A retarded release of the more hydrophilic metabolite is observed with respect to the substrate.

We believe that the described raspberry aspect of ketanone is not due to ketanone but derived from the perception of small amounts of its metabolite which is a low-threshold signature ingredient in raspberry aroma. Alternatively, the substrate may already have a weak raspberry aroma (higher olfactory threshold).

Example 6A

Suppressor of Enzyme That Metabolises 2-methoxyacetophenone

The procedure is performed as described in example 2 subject to the following modifications:

A volatile suppressor compound (inhibitor of nasal metabolic enzyme CYP2A13) is inhaled immediately prior to the inhalation of the test compound 2-methoxyacetophenone.

The test subject performs three runs in a row: (1) test compound only; (2) suppressor followed by test compound; (3) test compound only. Before and between runs, blank controls are recorded (inhalation of room air and recording of 30 inhalation/exhalation cycles).

In runs 1 and 3, the analysis shows a strong signal at m/z 137 corresponding to significant amounts of hydroxyacetophenone (metabolite).

In run (2) the m/z 137 signal (metabolite) is minor in comparison, showing that considerably less metabolite is formed in presence of the suppressor.

Example 6B

Suppressor of Enzyme that Metabolises Ketanone

The procedure is performed as described in example 6A, however, as a test compound ketanone is used and ketanone and its metabolite 4-(4-hydroxyphenyl)butan-2-one (raspberry ketone) are detected as described in example 5.

The results are analogous to example 6A. The run with suppressor shows a significantly decreased signal intensity for the metabolite 4-(4-hydroxyphenyl)butan-2-one (raspberry ketone).

Example 7

Metabo-GM, General Procedure

Exhaled compounds are trapped on a resin, followed by desorption of bound material and analysis by gas chromatography, linked to mass spectrometry (GC-MS).

A test subject inhales a saturated headspace of a known compound, and the exhaled air is trapped on an adsorbent Tenax™ TA resin.

A glass tube of 16 mm diameter is used. Said tube is filled with about 0.5 grams resin and silane-treated glass wool (Supelco, U.S.). Said wool is used at both sides of the resin to keep the resin in the middle of the tube. A test subject inhales the test compound, and slowly exhales through a tube that contains the resin. This is easily achieved by blocking one nostril and exhaling unilaterally through a tube connected to the open nostril. Trained test subjects able to inhale/exhale a fairly constant volume. In a first step, the test compound is placed in a container of about 0.75 litres. In a second step, saturated headspace is slowly inhaled and exhaled air is trapped using the resin. This step may be repeated, for example about 30 times, to increase the concentration of the volatile and metabolites on the adsorption resin. The optimal repeat rate needs to be adjusted for each test compound depending on vapour pressure and extent of metabolism. In a third step, a Thermoextractor (from GERSTEL, Germany) is used to transfer the compounds trapped on the resin to an analysis tube of smaller diameter (approximately 6 mm fits the Thermoextractor adaptor and fulfils standards for auto sampler loading). The analysis tube is loaded into an auto sampler in subsequent analysis. This step also removes water from the sample that may interfere with the subsequent analysis. In the fourth step, the analysis tube is placed in an auto sampler (Thermodesorption Autosampler TDS-A, GERSTEL, Germany) and a computer-controlled analysis sequence is started.

Said analysis encompasses 3 steps. First, the sample is cryo-focused in the GC injection liner by the thermal desorption of resin-bound compounds (Thermodesorption system TDS, GERSTEL, Germany) and concentrated in a Cryo-Trap (Cooled Injection System CIS, cooled with liquid nitrogen, GERSTEL, Germany) for subsequent heating and transfer to the separation column.

Then the compounds contained in the sample are separated by GC (Hewlett Packard Model 5890, equipped with a DB-Wax column, Macherey-Nagel, Germany) and analyzed by mass-spectrometry (Hewlett Packard Model 5972). Last, the MS patterns of the detected compounds are compared to databases to determine the chemical structure of the compounds.

Example 8

Metabo-GM, 2-methoxyacetophenone

The procedure is performed as described in example 7 with 2-methoxyacetophenone as test compound.

As a control, the headspace of the test compound is directly aspirated onto the resin. Only 2-methoxyacetophenone is found.

In exhaled breath of a test subject, in addition, 2-hydroxyacetophenone (metabolite) is detected with GC-MS.

Example 9

Metabo-GM, 2-methoxyacetophenone

The procedure is performed as described in example 7 and 8 subject to the following modification.

The test subject inhales and exhales differently.

In the first variant, inhalation and exhalation occur both through the mouth and exhaled air is slowly blown directly into the glass tube. In the second variant, inhalation occurs through the mouth and exhalation through the nose.

In the first variant minute amounts of 2-hydroxyacetophenone (metabolite) are found, however only in a small amount barely detectable. In the second variant (exhalation through nose), significantly more metabolite is detected.

This indicates that the respiratory tract metabolism of 2-methoxyacetophenone takes place predominantly as a result of enzymatic activity in the nasal cavity.

Example 10

Metabo-GM, Suppressor of Metabolism of 2-methoxyacetophenone

The procedure is performed as described in example 6A with a volatile suppressor that is inhaled prior to inhaling the test compound. The detection of test compound and metabolite is performed as described in example 7.

The test compound is 2-methoxyacetophenone.

In presence of the suppressor, only little amounts of 2-hydroxyacetophenone (metabolite) are detected, compared to the amount detected in its absence.

This confirms that the suppressor influences the formation of metabolites originating from the test compound which reaches the respiratory tract, more specifically the nasal cavity.

Example 11A

Metabo-GM, Styrallylacetate, Inhalation/Exhalation Through the Nose

The procedure is performed as described in example 7.

The test compound is styrallylacetate, which is an ester. An ester can potentially be hydrolysed to its metabolite by a hydrolase enzyme. For styrallylacetate, the metabolites styrallylalcohol and acetic acid are expected. This type of reaction is catalysed by an enzyme of the class of carboxyl esterases.

Significant amounts of styrallylalcohol and acetic acid (metabolites) are detected in the sample of exhaled air.

This indicates the presence of a carboxyl esterase activity in the respiratory tract which metabolized styrallylacetate to acetic acid and styrallylalcohol.

Example 11B

Metabo-GM, Styrallylacetate, Inhalation/Exhalation Through the Mouth

The procedure is performed as described in example 11A subject to the following modifications: The headspace of the test compound is inhaled and exhaled through the mouth as described in Experiment 9.

Less styrallylalcohol (metabolite) is detected compared to Example 11A, where inhalation and exhalation are performed through the nose (compared were the ratios of metabolite to substrate in order to compare the experiments). However, the amount of metabolite still is enough to be easily detectable by GC-MS indicating that carboxyl esterase activity is broadly distributed in the respiratory tract and not limited to the nasal cavity.

Example 12A

Metabo-GM, Phenethylacetate and Suppressor of Metabolism (Inhibitor of carboxyl esterase)

The procedure is performed as described in examples 7 and 10 subject to the following modifications:

As suppressor, an inhibitor for carboxyl esterase is used. As test compound, phenethylacetate is used, which is a substrate for carboxyl esterase.

In exhaled breath, phenethylalcohol is detected (metabolite). When inhaling the suppressor first, followed by inhaling the test compound, the proportion of detected metabolite is significantly lower (decreased to about 50%) compared to the analysis without the suppressor.

Example 12B

Metabo-GM, Styrallylacetate and Suppressor of Metabolism (Inhibitor of carboxyl esterase)

The procedure is performed as described in example 12A with an inhibitor for carboxyl esterase as suppressor, subject to the following modifications:

As test compound, styrallylacetate is used, which is a substrate for carboxyl esterase.

In exhaled breath, styrallylalcohol is detected (metabolite). When inhaling the suppressor first, followed by inhaling the test compound, the proportion of detected metabolite is significantly lower compared to the analysis without the suppressor. So there is a reduced rate of decrease of the test compound (enzyme substrate) in presence of the suppressor.

Example 13

Cascade Olfactometer, Identification of Modulator (Inhibitor)

A modulator is identified using an Olfactometer. As reference test compounds, odorant esters are used. A second test compound (potential modulator, modulator test compound) is tested in combination with these odorant test compounds. The odorant reference test compound is kept at a constant concentration with the modulator concentration being varied.

The reference test compound is the odorant styrallylacetate, which has a lower threshold than its metabolite styrallylalcohol. If metabolism is taking place, the amount of styrallylacetate which is stimulating the olfactory system is decreased. The finding of an enhanced intensity in presence of the modulator test compound by test subjects together with the finding of a reduced rate of decrease of styrallylacetate (substrate) but without an additional metabolite, as shown in example 12B for styrallylacetate, shows the presence of a modulator that is an inhibitor (i.e. metabolism is reduced in presence of the inhibitor and the substrate is either not or only slowly metabolised. In consequence, the metabolite is formed at a reduced rate.

A standard concentration (appropriate dilution of saturated headspace) of the odorant test compound is provided in one Olfactometer (cascade 1) as the reference, while in the second olfactometer (cascade 2) the odorant test compound is provided at the standard concentration supplemented with various concentrations of the modulator (appropriate dilutions of saturated headspace).

First, the threshold for the odorant styrallylacetate is determined for each test subject. The standard concentration is chosen so that it is perceived to be of week to moderate intensity as judged by each test subject.

The concentrations of the modulator test compound are chosen to be below the olfactory threshold of the test subject.

A sample is provided as headspace in a saturation chamber. The flow from said chamber is added to a carrier gas supply and mixed in a chamber which is connected with the sniffing port where a test subject detects the stimulus. Said flow (the headspace of the sample before addition to the carrier) is determined and adjusted so that the test subject rates said flow as medium intensity. This is the reference that is used in cascade 1. For styrallylacetate, a flow of 20 ml/min of the odorant is used.

In cascade 2, the odorant is provided at same flow as the reference (20 ml/min), and the flow of the added modulator test compound is varied between 1 to 900 ml/min in 6 dilution steps. Dilutions of an odorant test compound with a carrier gas are adjusted to provide a constant final concentration of an odorant test compound while the modulator test compound is varied in its final concentration.

In presence of the potential modulator, the test subject notes that the intensity of the odorant is increased.

The negative control (a solvent, in this case diethylphtalate) is used at the same flow as the potential modulator compound. The test subject does not note any difference in intensity when compared to the probe without potential modulator.

Example 14

Cascade Olfactometer, Identification of an Enhancing Compound

The analysis is performed as described in example 13 with the odorant styrallylacetate as test compound, subject to the following modifications: The odorant concentration in varied, while the modulator concentration is kept constant.

The effect of the modulator on the olfactory threshold of styrallylacetate is determined in as follows.

In cascade 1, a reference concentration of styrallylacetate slightly above the olfactory threshold of test subjects is used (20 ml/min).

In cascade 2, the styrallylacetate is present in combination with a constant concentration of the potential modulator (5 ml/min). The concentration styrallylacetate is varied by diluting the saturated headspace of the odorant (flow from 5-80 ml/min).

Test subjects compare cascade 1 (reference styrallylacetate), with cascade 2 (modulator+styrallylacetate at different concentration). For each pair (cascade 1 compared to 2) test subjects are asked to indicate whether the intensity is equal, higher, much higher, lower or much lower using a JND protocol (i.e. they indicate the "just noticeable difference").

For the comparison where the final concentration of styrallylacetate in cascade 1 and 2 is the same (20 ml/min), test subjects identify the odour intensity of the styrallylacetate sample in presence of the modulator compound at cascade 2 as stronger than the reference concentration at cascade 1.

For the negative control (diethylphtalate) the test subjects do not note any difference in intensity.

Alternatively, a dose response curve is recorded using one olfactometer (Cascade 2) by providing samples above and below the detected olfactory threshold of the test subjects. This is compared to the known threshold of the compound which is recorded beforehand.

Test subjects identify the olfactory threshold for styrallylacetate combined with the modulator as lower than the determined olfactory threshold for styrallylacetate alone.

The modulator test compound that was used is an inhibitor of carboxyl esterases and decreases the rate of ester hydrolysis. Consequently, the amount of ester available for stimulating the olfactory system is increased.

I claim:

1. Method of identifying or evaluating test compounds, wherein either the compound or at least one of its metabolite is an odorant, or a precursor of an odorant, or a modulator of the perception of an odorant, comprising
   a) Providing, in a container, a saturated, optionally diluted, headspace of a test compound,
   b) Inhaling said headspace by a test subject
   c) Exhaling exhaled breath by the test subject
   d) Analyzing the exhaled breath by a detection method selected from Metabo-GM, Metabospace, and Proton Transfer Reaction Mass Spectrometry (PTR-MS), or a combination thereof.

2. Method according to claim 1, wherein the test compound is inhaled and the exhaled breath is exhaled through the nose.

3. Method according to claim 1, wherein the test compound is inhaled through the nose and the exhaled breath is exhaled through the mouth.

4. Method according to claim 1, wherein the test compound is inhaled through the mouth and the exhaled breath is exhaled through the nose.

5. Method according to claim 1, wherein the test compound is inhaled and the exhaled breath is exhaled through the mouth.

6. Method according to claim 1 wherein in addition to the analysis by Metabo-GM, Metabospace, or Proton Transfer Reaction-Mass Spectrometry (PTR-MS), or a combination thereof an olfactometer analysis is performed.

7. Method according to claim 6, wherein the test compound is inhaled and the exhaled breath is exhaled through the nose.

8. Method according to claim 6, wherein the test compound is inhaled through the nose and the exhaled breath is exhaled through the mouth.

9. Method according to claim 6, wherein the test compound is inhaled through the mouth and the exhaled breath is exhaled through the nose.

10. Method according to claim 6, wherein the test compound is inhaled and the exhaled breath is exhaled through the mouth.

* * * * *